United States Patent [19]

Beck et al.

[11] Patent Number: 6,028,238

[45] Date of Patent: Feb. 22, 2000

[54] XYLENE ISOMERIZATION

[75] Inventors: Jeffrey Scott Beck, Burlington; Robert Andrew Crane, Jr., Monroeville; Jocelyn Anne Kowalski, Sewell, all of N.J.; Daria Nowakiwska Lissy, Glen Mills, Pa.; Mark Fischer Mathias, Pittsford, N.Y.; David Lawrence Stern, Mount Laurel, N.J.

[73] Assignee: Mobil Oil Corporation, Fairfax, Va.

[21] Appl. No.: 09/059,854

[22] Filed: Apr. 14, 1998

[51] Int. Cl.⁷ .................................. C07C 5/22; C07C 4/12
[52] U.S. Cl. ........................ 585/481; 585/482; 585/486
[58] Field of Search ................................. 585/481, 482, 585/486

[56] References Cited

U.S. PATENT DOCUMENTS

| 4,441,990 | 4/1984 | Huang | 208/111 |
|---|---|---|---|
| 5,516,956 | 5/1996 | Abichandani et al. | 585/481 |
| 5,689,027 | 11/1997 | Abichandani et al. | 585/481 |

*Primary Examiner*—Walter D. Griffin
*Assistant Examiner*—Thuan D. Dang
*Attorney, Agent, or Firm*—Peter W. Roberts; Malcolm D. Keen

[57] ABSTRACT

A process is described for isomerizing a feed which contains ethylbenzene and xylene, which process comprises the steps of:

(a) contacting the feed under ethylbenzene conversion conditions with a particulate first catalyst component which comprises a molecular sieve having a constraint index of 1–12, the particles of said first catalyst component having a surface to volume ratio of about 80 to less than 200 inch$^{-1}$ and the contacting step converting ethylbenzene in the feed to form an ethylbenzene-depleted product; and then (b) contacting the ethylbenzene-depleted product under xylene isomerization conditions with a second catalyst component.

10 Claims, No Drawings

XYLENE ISOMERIZATION

This invention is directed to a process for xylene isomerization using a multi-component catalyst system.

BACKGROUND OF THE INVENTION

Para-xylene is a valuable chemical feedstock which may be derived from mixtures of $C_8$ aromatics separated from such raw materials as petroleum naphthas, particularly reformates, usually by selective solvent extraction. The $C_8$ aromatic fractions from these sources vary quite widely in composition but will usually be in the range of 10 to 32 wt. % ethylbenzene (EB) with the balance, xylenes, being divided approximately 50 wt. % meta and 25 wt. % each of para and ortho.

Individual isomer products may be separated from the naturally occurring mixtures by appropriate physical methods. Ethylbenzene may be separated by fractional distillation, although this is a costly operation. Ortho-xylene may be separated by fractional distillation, and is so produced commercially. Para-xylene may be separated from the mixed isomers by fractional crystallization, selective adsorption (e.g., the Parex process), or membrane separation.

As commercial use of para-xylene has increased, combining physical separation with chemical isomerization of the other xylene isomers to increase the yield of the desired para-isomer has become increasingly important. However, since the boiling point of ethylbenzene is very close to those of para-xylene and meta-xylene, complete removal of ethylbenzene from the $C_8$ aromatic feed by distillation is impractical. Hence an important feature of any commercial xylene isomerization process is the ability convert ethylbenzene in the feed to useful by-products while simultaneously minimizing any conversion of xylenes to other compounds.

One commercially successful xylene isomerization process is described in U.S. Pat. No. 4,899,011 in which a $C_8$ aromatic feed, which has been depleted in its para-xylene content, is contacted with a two component catalyst system. The first catalyst component selectively converts the ethylbenzene by deethylation, while the second component selectively isomerizes the xylenes to increase the para-xylene content to a value at or approaching the thermal equilibrium value. The first catalyst component comprises a Constraint Index 1–12 molecular sieve, such as ZSM-5, which has an ortho-xylene sorption time of greater than 50 minutes based on its capacity to sorb 30% of the equilibrium capacity of ortho-xylene at 120° C. and an ortho-xylene partial pressure of 4.5±0.8 mm of mercury, whereas the second component comprises a Constraint Index 1–12 molecular sieve which has an ortho-xylene sorption time of less than 10 minutes under the same conditions. In one preferred embodiment, the first catalyst component is ZSM-5 having a crystal size of at least 1 micron and the second catalyst component is ZSM-5 having a crystal size of 0.02–0.05 micron. Each catalyst component also contains a hydrogenation component, preferably a platinum group metal.

An improvement over the process of U.S. Pat. No. 4,899,011 is described in U.S. Pat. No. 5,689,027 in which the first catalyst component in the two component system is preselectivated by coking, or more preferably by deposition of a surface coating of silica, to increase its ortho-xylene sorption time to greater than 1200 minutes under the same conditions as cited in the '011 patent. Using such a system it is found that high ethylbenzene conversion rates can be achieved with significantly lower xylene losses than obtained with the process of the '011 patent.

An object of the present invention is to further reduce the xylene losses obtainable with existing two component xylene isomerization processes such as those described in U.S. Pat. Nos. 4,899,011 and 5,689,027.

SUMMARY OF THE INVENTION

Accordingly, the invention resides in a process for isomerizing a feed which contains ethylbenzene and xylene, which process comprises the steps of:

(a) contacting the feed under ethylbenzene conversion conditions with a particulate first catalyst component which comprises a molecular sieve having a Constraint Index of 1–12, the particles of said first catalyst component having a surface to volume ratio of about 80 to less than 200 $inch^{-1}$, and the contacting step converting ethylbenzene in the feed to form an ethylbenzene-depleted product; and then (b) contacting the ethylbenzene-depleted product under xylene isomerization conditions with a second catalyst component.

Preferably, the particles of the first catalyst component have a surface to volume ratio of about 100 to about 150 $inch^{-1}$.

Preferably, the first catalyst component includes a hydrogenation component.

Preferably, the hydrogenation component of the first catalyst component is selected from platinum, palladium and rhenium.

Preferably, the second catalyst component comprises a molecular sieve having a Constraint Index of 1–12 combined with a hydrogenation component.

Preferably, the hydrogenation component of the second catalyst component is selected from platinum, palladium and rhenium.

Preferably, the first catalyst component has an ortho-xylene sorption time of greater than 50 minutes, and more preferably greater than 1200 minutes, based on its capacity to sorb 30% of the equilibrium capacity of ortho-xylene at 120° C. and an ortho-xylene partial pressure of 4.5±0.8 mm of mercury.

Preferably, the second catalyst component has an ortho-xylene sorption time of less than 50 minutes, and more preferably less than 10 minutes, based on its capacity to sorb 30% of the equilibrium capacity of ortho-xylene at 120° C. and an ortho-xylene partial pressure of 4.5±0.8 mm of mercury.

Preferably, the molecular sieve of the first catalyst component has an average crystal size in excess of 0.1 micron and the molecular sieve of the second catalyst component has an average crystal size less than 0.1 micron.

Preferably, the molecular sieve of the first catalyst component has an alpha value of greater than about 50 and the molecular sieve of the second catalyst component has an alpha value of less than about 50.

DETAILED DESCRIPTION OF THE INVENTION

Feedstock

In general, any aromatic $C_8$ mixture containing ethylbenzene and xylene may be used as feed to the process of this invention. Generally, such a mixture will typically have an ethylbenzene content in the approximate range of 5 to 60 weight percent, an ortho-xylene content in the approximate range of 0 to 35 weight percent, a meta-xylene content in the approximate range of 20 to 95 weight percent and a para-xylene range of 0 to 15 weight percent. The feed in addition to the above aromatic $C_8$ mixture may contain non-aromatic hydrocarbons, i.e., naphthenes and paraffins in an amount up to 30 weight percent. In a preferred embodiment, the invention provides means to process a mixture of $C_8$ aromatics such as that derived from catalytic reforming of a petroleum naphtha to a mixture of reduced ethylbenzene content and increased content of para-xylene. The invention is particularly effective in treating a para-xylene lean mixture of $C_8$ aromatics to increase the para-xylene concentration up to approximately the thermal equilibrium level.

The process of the present invention is especially suitable for the isomerization of $C_8$ aromatic streams that contain about 5 to 60 wt. % ethylbenzene, e.g., about 8 to 15 wt. % ethylbenzene. This range spans the range of ethylbenzene concentrations of streams that are derived from a reformer and a pyrolysis gasoline unit. The present catalyst may have high activity for cracking of normal and branched paraffins of the type present in unextracted $C_8$ aromatic streams.

Catalyst System

The catalyst system of the invention includes at least two catalyst components, the first of which has the primary function of selectively deethylating the ethylbenzene in the feedstream to benzene, while the second catalyst component selectively isomerizes xylenes in the feed. The first catalyst component can, and preferably will, effect some isomerization of the xylenes in the feed.

Each of the first and second catalyst components comprises an intermediate pore size molecular sieve which is characterized by a Constraint Index within the approximate range of 1 to 12 (e.g., less than about 7 Angstroms pore size, such as from about 5 to less than 7 Angstroms). The method by which Constraint Index is determined is described fully in U.S. Pat. No. 4,016,218, incorporated herein by reference for details of the method. Examples of intermediate pore size molecular sieves useful in this invention include ZSM-5 (U.S. Pat. Nos. 3,702,886 and Re. 29,948); ZSM-11 (U.S. Pat. No. 3,709,979); ZSM-12 (U.S. Pat. No. 3,832,449., ZSM-22 (U.S. Pat. No. 4,556,477); ZSM-23 (U.S. Pat. No. 4,076,842); ZSM-35 (U.S. Pat. No. 4,016,245); ZSM-38 (U.S. Pat. No. 4,406,859); ZSM-48 (U.S. Pat. No. 4,397,827); ZSM-57 (U.S. Pat. No. 4,046,685); and ZSM-58 (U.S. Pat. No. 4,417,780). The entire contents of the above references are incorporated by reference herein.

The molecular sieve of each of the first and second catalyst components is preferably associated with a hydrogenation-dehydrogenation component. Examples of such components include the oxide, hydroxide, sulfide, or free metal (i.e., zero valent) forms of Group 8 metals (i.e., Pt, Pd, Ir, Rh, Os, Ru, Ni, Co and Fe), Group 6 metals (i.e, Cr, Mo, W), Group 14 metals (i.e., Sn and Pb), Group 15 metals (i.e., Sb and Bi), and Group 7 metals (i.e., Mn, Tc and Re). Combinations of catalytic forms of such noble or non-noble metal, such as combinations of Pt with Sn, may be used. The metal is preferably in a reduced valence state, e.g., when this component is in the form of an oxide or hydroxide. The reduced valence state of this metal may be attained, in situ, during the course of a reaction, when a reducing agent, such as hydrogen, is included in the feed to the reaction.

In one preferred embodiment of the invention, the hydrogenation-dehydrogenation component is a noble metal (i.e., Pt, Pd, Ir, Rh, Os and Ru) and most preferably is platinum. In a further preferred embodiment of the invention, the hydrogenation-dehydrogenation component is an early transition metal, such as molybdenum, tungsten, rhenium and/or manganese, most preferably rhenium.

The hydrogenation/clehydrogenation component may be incorporated into the catalyst by methods known in the art, such as ion exchange, impregnation or physical admixture. For example, solutions of appropriate metal salts may be contacted with the remaining catalyst components, either before or after selectivation of the catalyst, under conditions sufficient to combine the respective components. The metal containing salt is preferably water soluble. Examples of such salts include chloroplatinic acid, tetraammineplatinum complexes, platinum chloride, tin sulfate and tin chloride. The metal may be incorporated in the form of a cationic, anionic or neutral complex such as $Pt(NH_3)_4^{2+}$ and cationic complexes of this type will be found convenient for exchanging metals onto the molecular sieve. For example, a platinum modified catalyst can be prepared by first adding the catalyst to a solution of ammonium nitrate in order to convert the catalyst to the ammonium form. The catalyst is subsequently contacted with an aqueous solution of tetraamine platinum(II) nitrate or tetraamine platinum(II) chloride. Anionic complexes such as the metatungstate, permanganate or perrhenate ions are also useful for impregnating metals onto the molecular sieves. After incorporation of the metal, the catalyst can then be filtered, washed with water and calcined at temperatures of from about 250 to about 500° C.

The amount of the hydrogenation-dehydrogenation component is suitably from about 0.001 to about 10 percent by weight, e.g., from about 0.1 to about 5 percent by weight, e.g, from about 0.1 to about 2 percent by weight, although this will, of course, vary with the nature of the component, with less of the highly active noble metals, particularly platinum, being required than of the less active base metals.

In practicing the process of the invention, it may be desirable to formulate either or both of the first and second catalyst components with another material resistant to the temperature and other conditions of the process. Such matrix materials include synthetic or naturally occurring substances as well as inorganic materials such as clay, silica, and/or metal oxides. The metal oxides may be naturally occurring or in the form of gelatinous precipitates or gels including mixtures of silica and metal oxides. Naturally occurring clays which can be composited with the molecular sieve include those of the montmorillonite and kaolin families, which families include the subbentonites and the kaolins commonly known as Dixie, McNamee, Georgia and Florida clays or others in which the main mineral constituent is halloysite, kaolinite, dickite, nacrite or anauxite. Such clays can be used in the raw state as originally mined or initially subjected to calcination, acid treatment or chemical modification.

In addition to the foregoing materials, the molecular sieves employed herein may be composited with a porous matrix material, such as alumina, silica-alumina, silica-magnesia, silica-zirconia, silica-thoria, silica-berylia, silica-titania, as well as ternary compounds such as silica-alumina-thoria, silica-alumina-zirconia, silica-alumina-magnesia, and silica-magnesia-zirconia. A mixture of these components could also be used. The matrix may be in the form of a cogel. The relative proportions of molecular sieve component and inorganic oxide gel matrix on an anhydrous basis may vary widely with the molecular sieve content ranging from between about 1 to about 99 percent by weight and more usually in the range of about 10 to about 80 percent by weight of the dry composite.

The first and second components of the catalyst system of the invention differ from each other in a number significant respects which ensure that first component selectively deethylates the ethylbenzene in the feedstream to benzene while the second component selectively isomerizes xylenes in the feed. These differing characteristics are discussed below In addition, the first and second components of the catalyst system of the invention may differ in their particulate form and size. Thus, as will be described in detail below, the first catalyst component is composed particles having a surface to volume ratio of about 80 to about 200 $inch^{-1}$, whereas the second catalyst component will typically be composed of particles with a surface to volume ratio less than 80 $inch^{-1}$.

Ethylbenzene Conversion Component

According to the invention, the first catalyst component, which selectively deethylates the ethylbenzene in the feedstream to benzene, is selected so as to have a surface to volume ratio of about 80 to <200 $inch^{-1}$, preferably about 100 to 150 $inch^{-1}$. Thus it has now been found that the ethylbenzene conversion reaction is sensitive to intraparticle (macroporous) diffusion limitations. By selecting the shape and size of the particles of the first catalyst component such that the surface to volume ratio is within the specified range, it is found that the intraparticle diffusion distance can be decreased without excessively increasing the pressure drop across the first catalyst bed. As a result, the xylene losses accompanying the ethylbenzene conversion in the first catalyst bed can be reduced, while at the same time the xylene isomerization activity of the first catalyst component can be increased. Producing a first catalyst component with the desired surface to volume ratio can readily be achieved by controlling the particle size of the catalyst or by using a shaped catalyst particle, such as the grooved cylindrical extrudate described in U.S. Pat. No. 4,328,130 or a hollow or solid polylobal extrudate as described in U.S. Pat. No. 4,441,990, the entire contents of both of which are incorporated herein by reference. For example, a cylindrical catalyst particle having a diameter of $\frac{1}{32}$ inch and a length of $\frac{3}{32}$ inch has a surface to volume ratio of 141, whereas a quadralobed solid extrudate having the external shape disclosed in FIG. 4 of U.S. Pat. No. 4,441,990 and having a maximum cross-sectional dimension of $\frac{1}{16}$ inch and a length of $\frac{3}{16}$ inch has a surface to volume ratio of 128. A hollow tubular extrudate having an external diameter of $\frac{1}{10}$ inch, an internal diameter of $\frac{1}{30}$ inch and a length of $\frac{3}{10}$ inch has a surface to volume ratio of 136.

In addition, the first catalyst component preferably has enhanced macroporosity which is achieved by adding a thermally decomposible organic material to the mix used to extrude the catalyst particles; and then calcining the extruded particles to remove the organic material. The thermally decomposible organic material can be any material which is compatible with the extrudalble mix used to form the catalyst particles and which is retained within the mass of the extruded catalyst particles but which can be removed from the catalyst particles by heating to leave macroporous voids within the particles. A suitable organic material is a cellulose such as that sold under the trade name Avicel.

The molecular sieve of the first catalyst component preferably has a higher acid activity than the molecular sieve of the second catalyst component. Thus molecular sieve of the first catalyst component preferably has an alpha value of at least 50 and typically has an alpha value of about 100 to about 500. Most preferably, the alpha value of the molecular sieve of the first catalyst component is between 100 and 300. The alpha test is described in U.S. Pat. No. 3,354,078; in the *Journal of Catalysis*, Vol. 4, p. 527 (1965); Vol. 6, p. 278 (1966); and Vol. 61, p. 395 (1980), each incorporated herein by reference as to that description. The experimental conditions of the test used herein include a constant temperature of 538° C. and a variable flow rate as described in detail in the *Journal of Catalysis*, Vol. 61, p. 395. The higher alpha values correspond with a more active cracking catalyst.

Each of the components of the catalyst system of the invention will normally exhibit mutually exclusive xylene diffusional properties. These properties can be identified by noting the time (in minutes) required to sorb 30% of the equilibrium capacity of ortho-xylene at 120° C. and at an ortho-xylene partial pressure of 4.5±0.8 mm of mercury, a test described in U.S. Pat. Nos. 4,117,026; 4,159,282; and Re. 31,782; each of which is incorporated by reference herein. The equilibrium capacity of ortho-xylene is defined herein as greater than 1 gram of xylene(s) per 100 grams of molecular sieve. In the catalyst system of the invention, the first catalyst component effective for ethylbenzene conversion preferably has an ortho-xylene sorption time (in minutes) in excess of about 50 and preferably greater than about 1200, but less than 10,000 minutes, while on the other hand, the second, isomerization component preferably has an ortho-xylene sorption time of less than about 50 minutes and preferably less than about 10 minutes.

The desired xylene diffusion properties of the first catalyst component can be achieved in a number of ways. For ortho-xylene diffusion times at or near the minimum value of 50 minutes, the selection of a large crystal form of the molecular sieve used in the catalyst, that is having an average crystal size in excess of 1 micron, may be sufficient. However, to achieve higher diffusivity values, it may be desirable to selectivate the first catalyst component by deposition on the surface of the catalyst particles of a layer of coke and/or an oxide, such as silica, which is inert under the process conditions experienced in use. Where the catalyst particles are selectivated, both large crystal size and medium crystal size (having a crystal size of 0.2–0.5 micron) molecular sieves can be used in the first catalyst component.

Where the first catalyst component is to be selectivated with silica, this is conveniently achieved by subjecting the catalyst to one or more treatments with an organosilicon compound in a liquid carrier, each treatment being followed by calcination of the treated material in an oxygen containing atmosphere, e.g., air. Such a multiple selectivation procedure is described in U.S. Pat. No. 5,476,823, the entire contents of which are incorporated herein by reference.

The organosilicon compound which is used to selectivate the first catalyst component may be, for example, a silicone, a siloxane, a silane or mixtures thereof These organosilicon compounds may have at least 2 silicon atoms per molecule. These organosilicon compounds may be solids in pure form, provided that they are soluble or otherwise convertible to the liquid form upon combination with the liquid carrier medium. The molecular weight of the silicone, siloxane or silane compound employed as a preselectivating agent may be between about 80 and about 20,000, and preferably within the approximate range of 150 to 10,000. Representative preselectivation silicone compounds include dimethyl silicone, diethyl silicone, phenylmethyl silicone, methylhydrogen silicone, ethylhydrogen silicone, phenylhydrogen silicone, methylethyl silicone, phenylethyl silicone, diphenyl silicone, methyltrifluoropropyl silicone, ethyltrifluoropropyl silicone, polydimethyl silicone, tetrachlorophenylmethyl silicone, tetrachlorophenylethyl silicone, tetrachlorophenylhydrogen silicone, tetrachlorophenylpbenyl silicone, methylvinyl silicone, and ethylvinyl silicone. The preselectivating silicone, siloxane or silane compound need not be linear, but may be cyclic, for example, hexamethyl cyclotrisiloxane, octamethyl cyclotetrasiloxane, hexaphenyl cyclotrisiloxane and octaphenyl cyclotetrasiloxane. Mixtures of these compounds may also be used as preselectivating agents, as may silicones with other functional groups.

Preferably, the kinetic diameter of the organosilicon compound, which is used to preselectivate the molecular sieve, is larger than the molecular sieve pore diameter, in order to avoid entry of the organosilicon compound into the molecular sieve pores and any concomitant reduction in the internal activity of the molecular sieve.

Preferred organosilicon preselectivating agents, particularly when the preselectivating agent is dissolved in an organic carrier or emulsified in an aqueous carrier, include dimethylphenyl methyl polysiloxane (e.g., Dow-550) and phenylmethyl polysiloxane (e.g., Dow-710). Dow-550 and Dow-710 are available from Dow Chemical Co., Midland, Mich.

Preferably, the liquid carrier for the organosilicon compound is an organic compound, such as a linear, branched or cyclic hydrocarbon having five or more, especially 7 or more, carbon atoms per molecule, e.g., an alkanes, such as heptane, octane, nonane or undecane. The boiling point of the organic compound, e.g., alkane, may be greater than about 70° C. Mixtures of low volatility organic compounds, such as hydrocracker recycle oil, may be employed as carriers. Particularly preferred organic carriers are decane and dodecane.

Following each impregnation with the organosilicon compound, the catalyst is calcined at a rate of from about 0.2° C./minute to about 5° C./minute to a temperature greater than 200° C., but below the temperature at which the crystallinity of the molecular sieve is adversely affected. This calcination temperature will generally be below 600° C. and preferably is within the approximate range of 350 to 550° C. The duration of calcination at the calcination temperature may be from 1 to 24 hours, e.g., from 2 to 6 hours.

In addition to, or in place of, silica selectivation, the first catalyst component may be subjected to coke selectivation. This optional coke selectivation typically involves contacting the catalyst with a thermally decomposable organic compound at an elevated temperature in excess of the decomposition temperature of said compound but below the temperature at which the crystallinity of the molecular sieve is adversely affected. This contact temperature may be, for example, less than about 650° C. Organic materials, which may be used for this coke selectivation process, encompass a wide variety of compounds including by way of example, hydrocarbons, such as paraffins, cycloparaffins, olefins, cycloolefins and aromatics; oxygen-containing organic compounds, such as alcohols, aldehydes, ethers, ketones and phenols; and heterocyclics, such as furans, thiophenes, pyrroles and pyridines. A hydrogen cofeed may be used to deter the excessive build-up of coke. Further details regarding coke selectivation techniques are provided in the U.S. Pat. No. 4,117,026, incorporated by reference herein. By using a combination of silica selectivation followed by coke selectivation, the number of organosilicon impregnation treatments required to achieve a particular xylene diffusivity can be reduced.

Isomerization Component

The second component of the catalyst system is effective to isomerize the xylenes of the feed containing $C_8$ aromatics. The second, isomerization component preferably has an ortho-xylene sorption time of less than about 50 minutes and preferably less than about 10 minutes. This is typically achieved by using a small crystal size molecular sieve, having an average crystal size of 0.02–0.05 micron, in this component. The molecular sieve of the second component of the catalyst system will typically have an alpha value less than about less than 50 and preferably from about 5 to about 25. The second component of the catalyst system may be prepared with the use of a thermally decomposible organic material so as to increase its macroporosity. In addition, the size and shape of the particles of the second catalyst component can be selected so as to have a surface to volume ratio of about 80 to <200 $inch^{-1}$, preferably about 100 to 150 $inch^{-1}$.

Process Conditions

The conditions used in the process of the invention are not narrowly defined, but generally will include a temperature of from about 400 to about 1,000° F., a pressure of from about 0 to about 1,000 psig, a weight hourly space velocity (WHSV) of between about 0.1 and about 200 $hr^{-1}$, and a hydrogen, $H_2$, to hydrocarbon, HC, molar ratio of between about 0.2 and about 10. Preferably, the conditions include a temperature of from about 650 to about 850° F., a pressure of from about 50 and about 400 psig, a WHSV of between about 3 and about 50 $hr^{-1}$ and a $H_2$ to HC molar ratio of between about 1 and about 5.

In general, the process of the invention is carried out in a fixed bed reactor containing the catalyst system described above. In a preferred embodiment, the first and second components of the catalyst system are in sequential beds in a single reactor. That is, the component of the catalyst system used in the process of the invention which is effective for ethylbenzene conversion forms a first bed, while the other component of the catalyst system, which is effective for xylene isomerization, forms a second bed downstream of the first bed. The feed is preferably cascaded from the first to the second bed without intervening separation of light gases. As an alternative, the first and second beds could be disposed in separate reactors which, if desired, could be operated at different process conditions. Additional catalyst beds may be provided prior or after the first and second catalyst components of the invention.

After the conversion process, the isomerization product can be treated to isolate para-xylene and/or other desirable xylene(s). Thus, for example, the isomerizate product can be fed to a variety of para-xylene recovery units, such as a crystalizer, a membrane separation unit, or a selective adsorption unit, and thus the para-xylene may be isolated and recovered. The residual isonmerizate can be stripped of products lighter than $C_8$. Products heavier than $C_8$ in the residual isomerizate can be further processed or may be fractionated out. $C_8$ fractions from which para-xylene has been removed can be recycled to the isomerizer.

One result of the process of this invention is to convert the mixed xylene components of the feed containing para-xylene in an amount less than that at thermal equilibrium to an extent such that product from the isomerizer contains para-xylene in an amount at least approaching that of para-xylene in the xylene mixture produced at thermal equilibrium.

Another result of the process of this invention is the conversion of a high proportion of the ethylbenzene contained in the mixed xylene feed. For example, ethylbenzene conversion levels of greater than about 30 wt %, typically greater than 50 wt % and even up to 90 wt %, can be accomplished. Due to the unique properties of the catalyst system used as a part of this invention, this e thylbenzene conversion is accomplished with little xylene loss, for example xylene loss levels of about 2.5% are easily achieved, e.g., xylene loss levels of about 1.5%, e.g., xylene loss levels of about 1.0% may also be achieved.

The invention will now be more particularly described with reference to the accompanying Examples.

EXAMPLE 1

A first catalyst component for a two-component catalyst system was formed from ZSM-5 having an average crystal size of about 1 micron. The ZSM-5 was composited with an alumina binder in a weight ratio of 65% ZSM-5 and 35% alumina binder. The mixture was extruded into cylindrical particles having a diameter of 1/16 inch and a length of 3/16 inch, with 0.1% Pt being addled during the mulling step, and was then steamed to an alpha of 150. The resultant whole extrudate, referred to herein as Catalyst A, had a surface to volume ratio of 77 $inch^{-1}$.

A sample of the whole extrudate was crushed and sized to 14/20 mesh. The resultant crushed extrudate, referred to herein as Catalyst B, had an average surface to volume ratio of about 150 $inch^{-1}$.

Catalysts A and B were used in ethylbenzene conversion/xylene isomerization evaluations on a $C_8$ aromatic feed consisting of 20 wt % ethylbenzene, 60 wt % meta-xylene and 20 wt % ortho-xylene. The evaluations were conducted in automated units each having a 3/8-inch diameter, stainless steel tube reactor and on-line GC sampling. 0.75 grams of catalyst was loaded into the reactor (with sand as inert packing material) and the catalyst sample was then heated in $N_2$ to 350° C. and reduced in hydrogen at this temperature for 2 hours. The reactor was then heated to reaction temperature, and feed was introduced after initially being percolated through alumina. Further details of the conditions of reaction and the results obtained are as summarized below in Table 1.

TABLE 1

| Catalyst | A | B | B |
|---|---|---|---|
| Conditions: | | | |
| WHSV | 20 | 40 | 20 |
| Temperature (° F.) | 800 | 800 | 800 |
| H2/HC | 1 | 1 | 1 |
| Pressure (psig) | 150 | 150 | 150 |
| Yields (wt. %) | | | |
| C5– | 3.6 | 3.8 | 4.4 |
| Benzene | 9.8 | 9.9 | 11.9 |
| Toluene | 2.9 | 1.6 | 2.9 |
| EB | 5.4 | 5.9 | 2.8 |
| Para Xylene | 17.0 | 17.9 | 18.2 |
| Meta Xylene | 42.5 | 42.2 | 41.0 |
| Ortho Xylene | 18.0 | 17.9 | 17.9 |
| C9+ | 1.0 | 0.7 | 0.8 |
| EB Conv (%) | 73 | 70 | 86 |
| Xylene Loss | 3.3 | 2.5 | 3.5 |
| Tol. + C9+ Make | 3.9 | 2.4 | 3.7 |
| Para Approach to Equilibrium (PATE) | 93.3 | 97.8 | 100.8 |

These results clearly show that the crushed catalyst had a higher activity for ethylbenzene conversion (EBC) at comparable severity than the base catalyst (86% for the crushed catalyst as compared with 73% for the base catalyst, both at 800° F./20 WHSV). At this higher EBC, the crushed catalyst afforded comparable xylene loss even though the EBC was higher. At comparable EBC (roughly 72% EBC), achieved at higher WHSV, the product slate was significantly improved, as shown by the lower xylene loss (3.3% xylene loss in the "whole extrudate case" vs. 2.5% for the crushed catalyst case). These results also show that the crushed catalyst had higher activity for xylene isomerization, as shown by the Para Approach To Equilibrium (PATE), than the base catalyst (100.8% PATE for the crushed catalyst vs. 93.3% PATE for the uncrushed catalyst, both at 800° F./20 WHSV).

EXAMPLE 2

A first catalyst component for a two-component catalyst system was formed from ZSM-5 having an average crystal size of about 0.2–0.5 micron. The ZSM-5 was composited with a silica binder in a weight ratio of 65% ZSM-5 and 35% silica binder. The silica-bound ZSM-5 was extruded into 1/16" diameter cylindrical particles using conventional means and was then subjected to a multiple silica-selectivation sequence involving with four successive impregnation treatments with 7.8 wt. % Dow-550 in decane. After each impregnation, the solvent was stripped, and the catalyst was calcined in $N_2$ and then in air to 538° C. Platinum was then incorporated onto the selectivated catalyst by incipient wetness impregnation with platinum tetraammine nitrate, followed by drying and air calcination. The resultant catalyst, designated herein as Catalyst C, contained 0.1 wt % platinum and had a surface to volume ratio of 77 $inch^{-1}$.

A sample of the whole extrudate was crushed and sized to 14/20 mesh. The resultant crushed extrudate, referred to herein as Catalyst D, had an average surface to volume ratio of about 150 $inch^{-1}$.

Catalysts C and D were used in ethylbenzene conversion/xylene isomerization evaluations described in Example 1 and the results are summarized in Table 2.

TABLE 2

| Catalyst | C | D | D |
|---|---|---|---|
| Conditions: | | | |
| Temperature (° F.) | 800 | 780 | 800 |
| WHSV (Hr-1) | 20 | 40 | 20 |
| Pressure (psig) | 150 | 150 | 150 |
| H2/HC | 1 | 1 | 1 |
| Yields (wt. %): | | | |
| C5– | 2.9 | 4.2 | 5.4 |
| Benzene | 10.4 | 12.0 | 14.1 |
| Toluene | 0.7 | 0.3 | 0.9 |
| Ethylbenzene | 6.2 | 3.3 | 0.6 |
| Para Xylene | 0.3 | 0.4 | 0.6 |
| Meta Xylene | 59.4 | 59.6 | 58.6 |
| Ortho Xylene | 19.9 | 20.1 | 19.8 |
| C9+ | 0.1 | 0.1 | 0.1 |
| EB Conversion (%) | 69 | 84 | 97 |
| Xylene Loss | 0.5 | 0 | 1.3 |
| Toluene + C9+ Make | 0.8 | 0.4 | 1.0 |

As was demonstrated above with the non-selectivated catalyst, the performance of the crushed catalyst was superior to the "whole extrudate" catalyst. Thus, at comparable severity (800° F., 20 WHSV), the whole extrudate achieved 69% EBC while the crushed catalyst achieved 97% EBC. At less severe conditions (780° F., 40 WHSV), the crushed catalyst still achieved higher EBC than the whole extrudate catalyst (84% EBC vs. 69% EBC) and, further, the product slate was superior to that afforded by the whole extrudate catalyst (xylene loss of 0.5% for the whole extrudate at 69% EBC vs. 0% for the crushed catalyst at 84% EBC).

EXAMPLE 3

(a) The first catalyst component for a two-component catalyst system was prepared by dry mixing ZSM-5 crystals having an average of crystal size of about 1 micron with alumina in proportions to give 50:50 molecular sieve/Al2O3 on a 100% solids basis. Water was added to form an extrudable mull which was then extruded on a Bonnot extruder to produce solid, cylindrical particles having a diameter of 1/16 inch and a length of 3/16 inch so that the surface to volume ratio of the particles was 77 inch$^{-1}$. The extruded particles were dried at 250° F. and then calcined in nitrogen at 1000° F. for 3 hours. The calcined extrudate was humidified and then exchanged twice with 1N NH4NO3 (5 ml solution/gm extrudate), rinsed with deionized water, dried at 250° F., and calcined in air at 1000° F. for 6 hours. The resultant catalyst was impregnated via incipient wetness technique with a rhenium solution prepared by dissolving rhenium (VII) oxide in deionized water. The rhenium-impregnated catalyst was dried at 250° F., calcined in air at 660° F. for 3 hours and then steamed at 900° F. for 3.5 hours. The first catalyst component is designated Catalyst E.

The above procedure was then repeated to prepare the second catalyst component for the system, but the ZSM-5 crystals employed had an average of crystal size of 0.02–0.05 micron. The final rhenium impregnated second catalyst component is designated Catalyst F.

(b) The procedure outlined in (a) above was repeated to produce a second two component catalyst system but, in the case of the first catalyst component, 10 wt % Avicel PH-200, a burnout agent, was added to the extrusion mix and the mix was extruded into a solid quadrulobe extrudate having a maximum cross-sectional dimension of 1/16 inch, a length of 3/16 inch and a surface to volume ratio of 128 inch$^{-1}$. After rhenium impregnation, the resultant quadrulobe-shaped first catalyst component is designated Catalyst G.

Each of the two component catalyst systems was used to conduct the ethylbenzene conversion/xylene isomerization evaluations on a $C_8$ aromatic feed consisting of 20 wt % ethylbenzene, 60 wt % meta-xylene and 20 wt % ortho-xylene. The evaluations were conducted in automated units each having a 3/8-inch diameter, stainless steel tube reactor and on-line GC sampling. 0.5 g of the first component was stacked in the reactor as a "top bed catalyst" over 1.5 g of the second component as a bottom bed catalyst, using sand as inert packing material. The catalyst system was then heated in $N_2$ to 350° C. and reduced in hydrogen at this temperature for 2 hours. The reactor was then heated to reaction temperature, and feed was introduced after initially being percolated through alumina. Further details of the conditions of reaction and the results obtained are as summarized in the Table 3.

TABLE 3

| Top Bed Catalyst | E | G |
|---|---|---|
| Weight of Top Bed | 0.5 g | 0.5 g |
| Bottom Bed Catalyst | F | F |
| Weight of Bottom Bed | 1.5 g | 1.5 g |
| Temperature (F) | 800 | 780 |
| H2/HC | 2 | 2 |
| WHSV | 10 | 10 |
| Pressure (psig) | 200 | 200 |
| Yields (wt. %) | | |
| C5− | 1.7 | 1.7 |
| Benzene | 4.6 | 4.7 |
| Toluene | 1.9 | 1.5 |
| Ethylbenzene | 3.0 | 2.9 |
| Para Xylene | 21.0 | 21.1 |
| Meta Xylene | 46.1 | 46.6 |
| Ortho Xylene | 20.6 | 20.5 |
| C9+ | 1.2 | 0.9 |
| EB Conversion | 70.6 | 71.5 |
| Xylene Loss | 2.4 | 1.8 |
| Toluene + C9+ Yield | 3.0 | 2.4 |
| Para Approach to Equil. (PATE) | 102.0 | 102.5 |

The above results show that the catalyst system having the top bed catalyst which is shaped such that its surface to volume ratio is 80 to <200 inch$^{-1}$ and which was extruded with organic had superior performance as compared to system in which a catalyst having a surface to volume ratio <80 inch$^{-1}$ and extruded without organic was used for the top bed. This is evident from the 20° F. lower reaction temperature required for similar ethylbenzene conversion (780 vs. 800° F.) and the lower xylene loss (1.8% vs. 2.4%), in addition to other yield slate improvements.

What we claim is:

1. A process for isomerizing a feed which contains ethylbenzene and xylene, which process comprises the steps of:
   (a) contacting the feed under ethylbenzene conversion conditions with a particulate first catalyst component which comprises a molecular sieve having a Constraint Index of 1–12, the particles of said first catalyst component having a surface to volume ratio of 128 to 150 inch$^{-1}$ and the contacting step converting ethylbenzene in the feed to form an ethylbenzene-depleted product; and then
   (b) contacting the ethylbenzene-depleted product under xylene isomerization conditions with a second catalyst component.

2. The process of claim 1, wherein the first catalyst component includes a hydrogenation component.

3. The process of claim 2, wherein the hydrogenation component of the first catalyst component is selected from platinum, palladium and rhenium.

4. The process of claim 1, wherein the first catalyst component has an ortho-xylene sorption time of greater than 50 minutes, based on its capacity to sorb 30% of the equilibrium capacity of ortho-xylene at 120° C. and an ortho-xylene partial pressure of 4.5±0.8 mm of mercury.

5. The process of claim 1, the second catalyst component comprises a molecular sieve having a Constraint Index of 1–12 combined with a hydrogenation component.

6. The process of claim 5, wherein the hydrogenation component of the second catalyst component is selected from platinum, palladium and rhenium.

7. The process of claim 5, wherein the second catalyst component has an ortho-xylene sorption time of less than 50 minutes, based on its capacity to sorb 30% of the equilibrium capacity of ortho-xylene at 120° C. and an ortho-xylene partial pressure of 4.5±0.8 mm of mercury.

8. The process of claim 1, wherein at least the first catalyst component is produced by mixing the molecular sieve thereof with a thermally decomposable organic component and, after forming the resulting mixture into particles, heating the particles to decompose said organic material.

9. The process of claim 1, wherein the molecular sieve of the first catalyst component has an alpha value of greater than about 50 and the molecular sieve of the second catalyst component has an alpha value of less than about 50.

10. A process for isomerizing a feed which contains ethylbenzene and xylene, which process comprises the steps of:

(a) contacting the feed under ethylbenzene conversion conditions with a particulate first catalyst component which comprises a molecular sieve having a Constraint Index of 1–12, the contacting step converting ethylbenzene in the feed to form an ethylbenzene-depleted product, and the particles of said first catalyst component having a surface to volume ratio within the range of 128 to 150 inch$^{-1}$ such that the xylene losses during the contacting step are less than that those which would be obtained with a first catalyst component having a surface to volume ratio outside said range; and then (b) contacting the ethylbenzene-depleted product under xylene isomerization conditions with a second catalyst component.

* * * * *